(12) United States Patent
Dovesi et al.

(10) Patent No.: US 6,514,257 B2
(45) Date of Patent: Feb. 4, 2003

(54) DEVICE FOR ANCHORING AN ELONGATED TENSILE FLEXIBLE ELEMENT FOR RECONSTRUCTION OF A TORN LIGAMENT

(75) Inventors: Alan Dovesi, Bologna (IT); Franco Mingozzi, Calderara Di Reno (IT)

(73) Assignee: Citieffe S.r.l., Calderara Di Reno (IT)

( * ) Notice: Subject to any disclaimer, the term of this patent is extended or adjusted under 35 U.S.C. 154(b) by 0 days.

(21) Appl. No.: 09/899,034

(22) Filed: Jul. 6, 2001

(65) Prior Publication Data

US 2002/0165547 A1 Nov. 7, 2002

(30) Foreign Application Priority Data

May 2, 2001 (IT) .................................. BO2001A000263

(51) Int. Cl.[7] .......................... A61B 17/58; A61B 17/60; A61F 2/00; A61F 2/32; A61F 2/34; A61F 2/36; A61F 2/38; F61B 37/12
(52) U.S. Cl. .............................. 606/73; 606/60; 606/72; 606/104; 606/99; 411/438; 623/13.14; 623/13.12; 623/13.13; 623/13.11
(58) Field of Search ............................ 606/60, 72, 73, 606/104, 99; 411/438; 623/13.14, 13.12, 13.13, 13.11

(56) References Cited

U.S. PATENT DOCUMENTS

| 4,309,135 | A | * | 1/1982 | Gutshall ...................... 411/17 |
| 4,708,132 | A | | 11/1987 | Thomas |
| 4,712,955 | A | * | 12/1987 | Reece et al. .................. 411/17 |
| 5,006,023 | A | * | 4/1991 | Kaplan .......................... 411/17 |
| 5,662,683 | A | * | 9/1997 | Kay ............................. 606/232 |
| 5,961,520 | A | * | 10/1999 | Beck, Jr. et al. .............. 606/72 |
| 5,964,772 | A | * | 10/1999 | Bolduc et al. .............. 606/142 |
| 6,276,883 | B1 | * | 8/2001 | Unsworth et al. .......... 411/324 |

FOREIGN PATENT DOCUMENTS

| WO | 97 07744 | 3/1997 |
| WO | 01 28457 | 4/2001 |

* cited by examiner

*Primary Examiner*—Gregory Huson
*Assistant Examiner*—Anuradha Ramana
(74) *Attorney, Agent, or Firm*—Guido Modiano; Albert Josif; Daniel O'Byrne

(57) ABSTRACT

A device for anchoring an end of an elongated tensile flexible element guided along a tunnel provided through the bones of a joint for reconstruction of a ligament, comprising a female element, which defines an internal thread and can be inserted in the tunnel, and a male element, which defines an external thread and is suitable to be screwed with play into the female element so as to secure the elongated element between the internal and external threads.

9 Claims, 3 Drawing Sheets

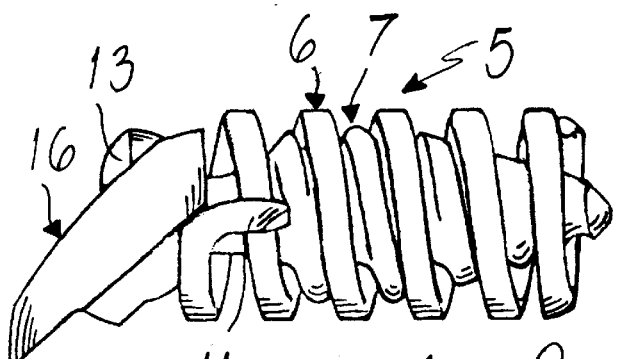
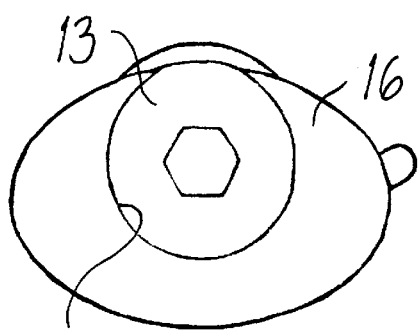
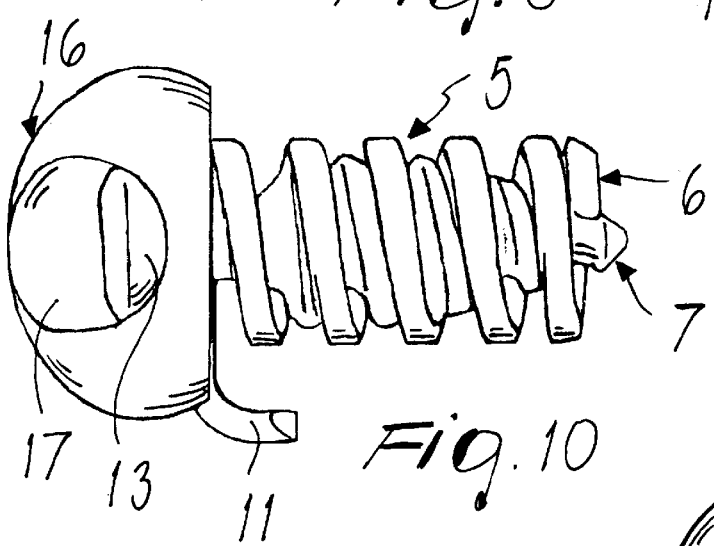
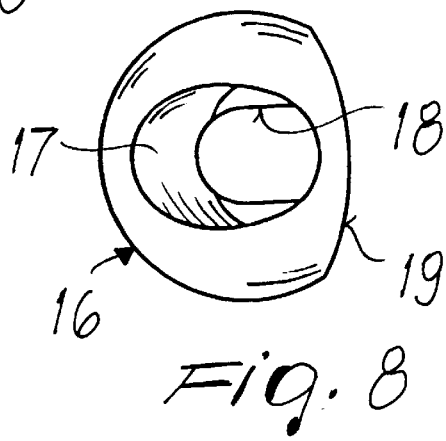
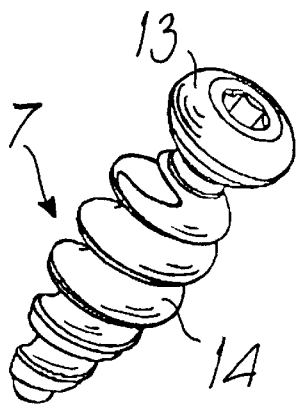
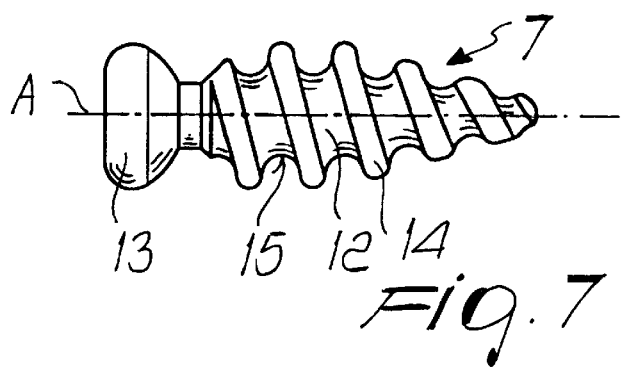

DEVICE FOR ANCHORING AN ELONGATED TENSILE FLEXIBLE ELEMENT FOR RECONSTRUCTION OF A TORN LIGAMENT

BACKGROUND OF THE INVENTION

The present invention relates to a device for anchoring the end of an elongated tensile flexible element, such as a natural or synthetic tendon, in the reconstruction of a torn ligament.

The device is designed to be used in the reconstruction of ligaments of limb joints, such as for example the anterior cruciate ligament of the knee joint.

The methods currently used for reconstructing the ligaments of a joint entail forming a tunnel through the ends of the bones to be connected and inserting in such tunnel an elongated element which is at once tensile and flexible and is fixed, by means of its opposite ends, at the openings of the tunnel by way of staples or other devices. The elongated element can be constituted by a gracilis tendon or semitendinosus tendon taken from the patient or by a string of synthetic filaments.

Known reconstruction methods suffer some shortcomings mostly linked to the anchoring of the ligaments. Ligament anchoring is in fact generally performed by means of staples located on the external cortex, such staples being inherently quite bulky. Moreover, external anchoring entails leaving a considerable length.

SUMMARY OF THE INVENTION

The aim of the present invention is to provide an anchoring device which allows to obviate the drawbacks currently suffered in the reconstruction of joint ligaments.

Within this aim, an object of the present invention is to provide an anchoring device which is simple and inexpensive to manufacture and which can be applied easily and quickly.

This aim and this and other objects which will become better apparent hereinafter are achieved by a device for anchoring an end of an elongated tensile flexible element guided along a tunnel formed through the bones of a joint for reconstruction of a ligament, comprising a female element, which defines an internal thread and can be inserted in said tunnel, and a male element, which defines an external thread and is adapted to be screwed with play into said female element so as to secure said elongated element between said internal and external threads.

According to another embodiment of the invention, the female element is constituted by a filament which is coiled so as to define a cylindrical helix which forms said internal thread and whose pitch is complementary to the pitch of the external thread of said male element.

In still another embodiment of the invention, the male element has a thread whose turns lie around a convex core.

BRIEF DESCRIPTION OF THE DRAWINGS

Further characteristics and advantages of the invention will become better apparent from the following description of a preferred embodiment thereof, illustrated only by way of non-limitative example in the accompanying drawings, wherein:

FIGS. 6 and 7 are respectively a perspective view and a side view of the male element;

FIG. 8 is a view of a washer to be associated with the male element;

FIGS. 9 and 10 are two different side views of the device, illustrating the position assumed by the female element and the male element and by the washer in the anchoring condition of FIG. 1;

FIG. 11 is an axial view of the device.

DESCRIPTION OF THE PREFERRED EMBODIMENTS

Figure 1:
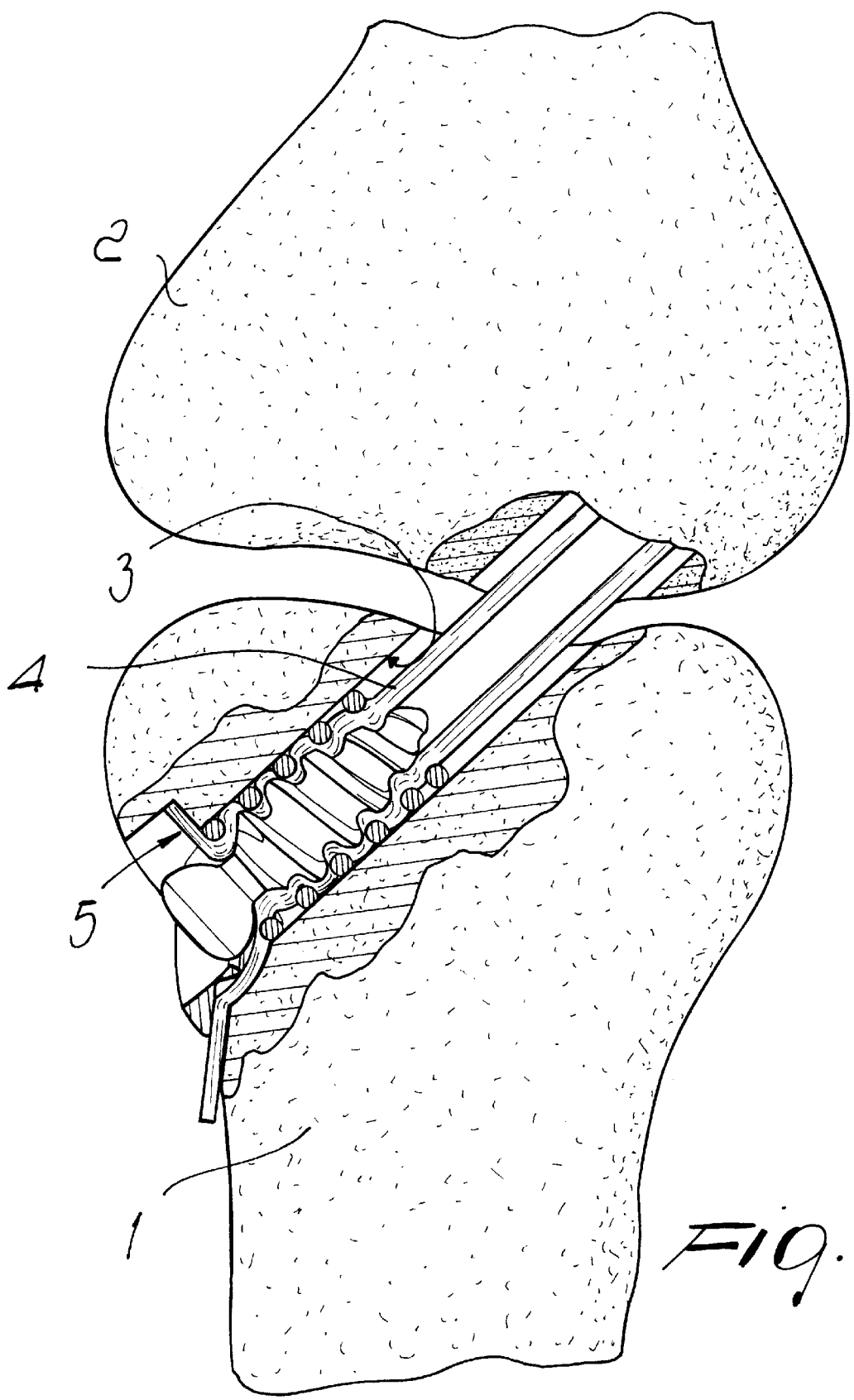
FIG. 1 is a partially sectional view of the device in the anchoring condition.

With reference to the figures, the reference numerals 1 and 2 designate the heads of the two bones that form the articulation whose ligaments are to be reconstructed. For the sake of illustration, it is assumed for example that the heads 1 and 2 are respectively the heads of the tibia and of the femur and that the ligament to be reconstructed is the anterior cruciate ligament.

According to known methods which are not included within the scope of the present invention and therefore are not described, a cylindrical tunnel 3 is provided through the heads 1 and 2 of the tibia and of the femur, and an elongated tensile flexible element is guided through the tunnel as a replacement for the torn ligament. Such elongated element is constituted by a natural or synthetic tendon 4 whose anchoring inside the tunnel 3 is performed by the device according to the present invention.

Such device is generally designated by the reference numeral 5 in FIGS. 9 and 10 and comprises a female element 6 and a male element 7.

Figure 3:
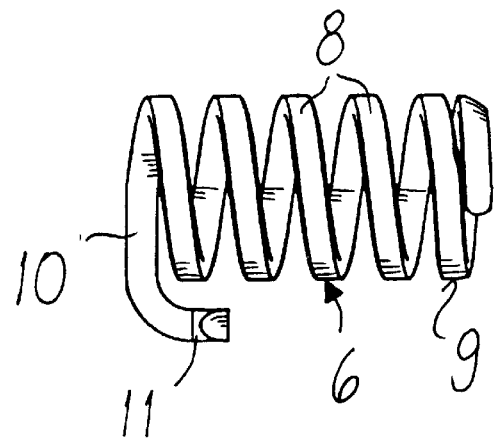
FIGS. 2, 3 and 4 are respectively a perspective view, a side view and a sectional view of the female element.
Figure 4:
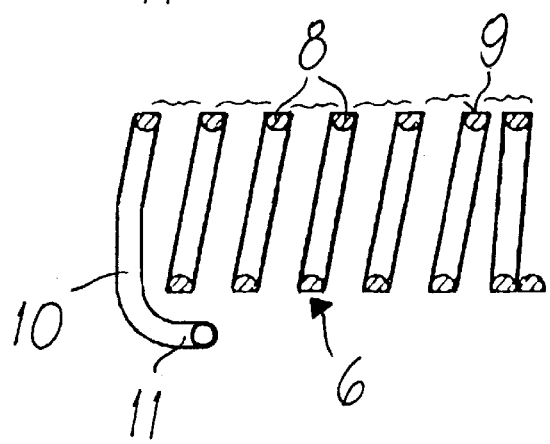
Figure 2:
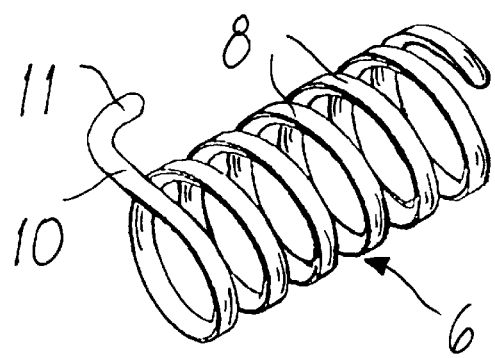

The female element 6 (FIGS. 2–4) is constituted by a sort of cylindrical cage formed by means of a filament which is coiled so as to define a cylindrical helix composed of turns 8 which have a constant pitch. The turns 8 form an internal thread which is adapted to accommodate the male element 7 by screwing. Conveniently, the turns 8 have an external flat region 9 which facilitates the insertion of the element 6 in the tunnel 3. In order to prevent the element 6 from rotating inside the tunnel 3, the turn located at the end designed to remain proximate to the inlet of the tunnel 3 is extended by a tangential part 10 ending with a portion 11 which is folded axially and by means of which a rotation-preventing anchoring is achieved on the cortex of the bone.

The male element 7 (FIGS. 6 and 7) is constituted by a screw which has an axis A and is composed of a core or shank 12 provided with a hemispherical head 13. The shank 12 has a convex shape and a thread 14 runs around it with a pitch which is equal to the pitch of the female element 6 and has a semicircular cross-section narrower than the distance that separates the turns 8 of the female element 6.

The turns of the thread 14 are separated by a tunnel 15 having a semicircular cross-section which is narrower than the diameter of the filament of which the female element 6 is made.

The disclosed device is completed by a washer 16 constituted by a disk which is convex like a spherical dome and has a cavity 17 whose dimensions are such that it can accommodate the head 13 of the male element 7. In the bottom of the cavity 17 an opening 18 is provided through which the shank 12 of the male element is guided. The opening 18 extends diametrically in order to give the male element 7 a certain freedom of movement with respect to the washer 16. The cavity 17 has a spherical shape complementary to the shape of the head 13 of the male element 7. In this manner, the washer 16 can be orientated with respect to the axis A in order to adapt perfectly to the cortex of the bone. A chamfer 19 of the washer 16 facilitates its inclination without interfering with the female element 6.

Figure 5:
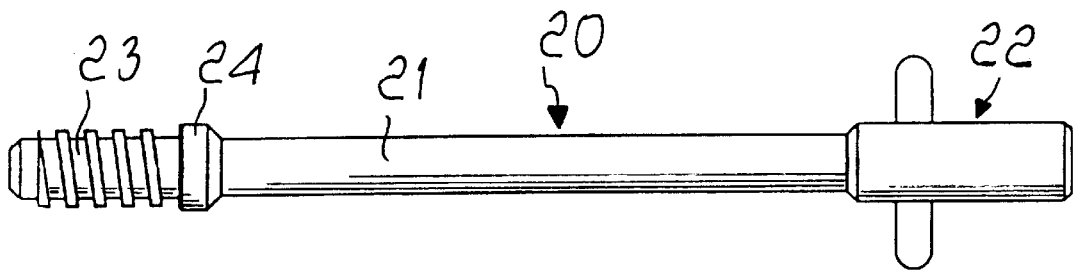
FIG. 5 is a view of a tool for applying the female element in the bone tunnel.

The device is applied by first inserting the female element 6 in the tunnel 3. This can be achieved by means of a tool 20 which is shown in FIG. 5 and is composed of a shank 21 having, at one end, a handle 22 and, at the opposite end, a threaded portion 23 suitable to be screwed into the female element 6 until it abuts against a collar 24.

After positioning the female element 6 in the tunnel 3 so that the portion 11 anchors in the cortex of the bone 1, the new tendon 4 is guided therethrough so that its end portions protrude from the tunnel 3. Finally, the male element is inserted by screwing and, thanks to its convex shape, forces the tendon T to engage between the turns 8 of the female element, while the washer 16, by abutting against the cortex, blocks its end portions.

The device according to the invention allows to obtain a double substantial advantage. First of all, a firm anchoring of the tendon is provided thanks to the fact that such tendon, by being arranged between the turns 8 of the female element and the thread 14 of the male element 7, follows a winding path which offers considerable resistance to traction stresses, which is added to the resistance provided by the clamping between the thread 14 and the turns 8.

Secondly, the anchoring of the tendon occurs inside the bone, so that the length of the tendon is reduced significantly, with particular advantages during the step of inclusion of the tendon in the bone, since the slack of the tendon in the tunnel 3 is reduced.

In the practical execution of the device according to the invention, the shapes and the dimensions of the components may vary according to requirements.

The device can be made of metal (titanium or steel) or of composite, absorbable or shape-memory materials.

The disclosures in Italian Patent Application No. BO2001A000263 from which this application claims priority are incorporated herein by reference.

What is claimed is:

1. A device for anchoring an end of an elongated tensile flexible element guided along a tunnel formed through the bones of a joint for reconstruction of a ligament, comprising a female element, which defines an internal thread and can be inserted in said tunnel, and a male element, which defines an external thread and is adapted to be screwed with play into said female element so as to secure said elongated element between said internal and external threads.

2. The device according to claim 1, wherein said female element is constituted by a cylindrical cage made of a filament having a circular cross-section which is coiled so as to define a cylindrical helix whose turns form a thread.

3. The device according to claim 2, comprising a tool which comprises a shank having a handle at one end and, at an opposite end, a threaded portion which is suitable to be screwed into said cage until it abuts against a collar of said shank.

4. The device according to claim 2, wherein said turns are flattened externally.

5. The device according to claim 2, wherein the turn located at an end that lies proximate to an inlet of said tunnel has an extension which forms an axial end portion suitable to engage the cortex of the bone.

6. The device according to claim 1, wherein said male element is constituted by a convex screw having a thread having a pitch equal to a pitch of said internal thread defined by the turns of said female element.

7. The device according to claim 6, wherein the thread of said screw has a semicircular cross-section whose diameter is smaller than a distance that separates the turns of said female element.

8. The device according to claim 6, wherein said screw has a head which is hemispherical on a side directed toward the internal thread of the female element.

9. The device according to claim 8, wherein on said screw a convex washer is provided having a cavity which is suitable to accommodate the head of said screw and is provided with an opening which lies diametrically for the passage of said screw.

\* \* \* \* \*